US009290424B2

(12) United States Patent
Cottrell et al.

(10) Patent No.: US 9,290,424 B2
(45) Date of Patent: Mar. 22, 2016

(54) PROCESSES FOR THE HYDROGENATION OF HALOGENATED ALKENES AND THE MANUFACTURE OF FLUORINATED OLEFINS

(71) Applicant: HONEYWELL INTERNATIONAL INC., Morristown, NJ (US)

(72) Inventors: Stephen A. Cottrell, Baton Rouge, LA (US); John J. Senetar, Naperville, IL (US); Hsueh S. Tung, Getzville, NY (US); Daniel C. Merkel, West Seneca, NY (US); Yuon Chiu, Denville, NJ (US); Haluk Kopkalli, Staten Island, NY (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 0 days.

(21) Appl. No.: 13/827,302

(22) Filed: Mar. 14, 2013

(65) Prior Publication Data

US 2014/0275645 A1    Sep. 18, 2014

(51) Int. Cl.
C07C 17/354  (2006.01)
C07C 17/25   (2006.01)

(52) U.S. Cl.
CPC .............. *C07C 17/354* (2013.01); *C07C 17/25* (2013.01)

(58) Field of Classification Search
CPC ...... C07C 17/354; C07C 19/08; C07C 21/18; B01J 23/44
USPC ......................................................... 570/175
See application file for complete search history.

(56) References Cited

U.S. PATENT DOCUMENTS

| 5,679,875 | A  | 10/1997 | Aoyama et al. |
| 5,714,654 | A  | 2/1998  | Yamamoto et al. |
| 6,011,189 | A  | 1/2000  | Blanpied et al. |
| 7,560,602 | B2 | 7/2009  | Van Der Puy et al. |
| 8,013,194 | B2 | 9/2011  | Chiu et al. |
| 8,329,964 | B2 | 12/2012 | Devic et al. |
| 8,389,779 | B2 | 3/2013  | Avril et al. |
| 2007/0179324 | A1 | 8/2007 | Van Der Puy et al. |
| 2009/0131727 | A1 | 5/2009 | Yang et al. |
| 2010/0029997 | A1 | 2/2010 | Wang et al. |
| 2011/0021849 | A1 | 1/2011 | Avril et al. |

(Continued)

FOREIGN PATENT DOCUMENTS

| CN | 102066295 A | 5/2011 |
| CN | 101628850 B | 9/2012 |

(Continued)

OTHER PUBLICATIONS

WO2010142877A1; Dec. 2010; pp. 1-4; English translation.*
WO2010142878A1; Dec. 2010; pp. 1-4; English translation.*
PCT ISR & Written Opinion issued in PCT/US2014/021482 dated Jun. 20, 2014.

*Primary Examiner* — Jafar Parsa
*Assistant Examiner* — Medhanit Bahta
(74) *Attorney, Agent, or Firm* — Bruce Bradford

(57) ABSTRACT

In certain aspects, the present invention relates to methods for increasing the cost efficiency and safety of the hydrogenation of a fluorinated olefin by controlling the reaction conditions and parameters. In further aspects, the hydrogenation reaction is provided in a two stage reaction wherein the reactant amounts, temperature and other parameters are controlled such that the conversion percentage, selectivity, and reaction parameters are all within commercially acceptable levels.

18 Claims, 1 Drawing Sheet

(56) References Cited

U.S. PATENT DOCUMENTS

| | | |
|---|---|---|
| 2011/0112338 A1 | 5/2011 | Smith et al. |
| 2011/0152586 A1 | 6/2011 | Low et al. |
| 2011/0190554 A1 | 8/2011 | Pigamo et al. |
| 2012/0101314 A1 | 4/2012 | Devic et al. |
| 2012/0101315 A1 | 4/2012 | Devic et al. |
| 2012/0301373 A1 | 11/2012 | Chiu et al. |

FOREIGN PATENT DOCUMENTS

| | | | |
|---|---|---|---|
| CN | 101628849 B | | 10/2012 |
| CN | 101628851 B | | 10/2012 |
| WO | WO 2010142877 A1 | * | 12/2010 |
| WO | WO 2010142878 A1 | * | 12/2010 |

* cited by examiner

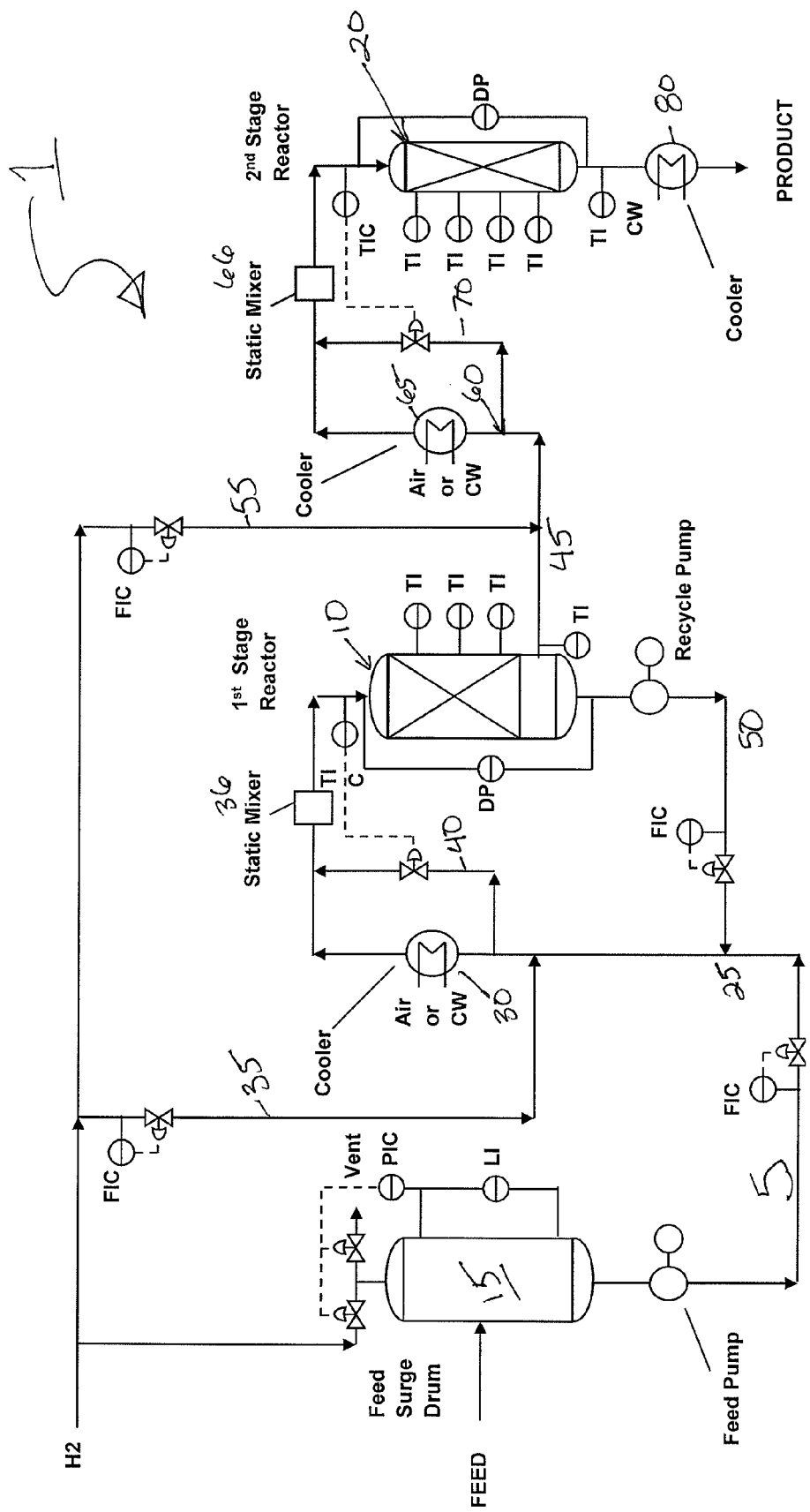

PROCESSES FOR THE HYDROGENATION OF HALOGENATED ALKENES AND THE MANUFACTURE OF FLUORINATED OLEFINS

FIELD OF THE INVENTION

The present invention relates to processes for producing haloalkenes, particularly, though not exclusively, 2,3,3,3-tetrafluoropropane (HFO-1234yf) and/or 1,2,3,3,3-pentafluoropropene (HFO-1225ye).

BACKGROUND OF THE INVENTION

Chlorine-containing compounds, such as chlorofluorocarbons (CFCs), have been employed as refrigerants, foam blowing agents, cleaning agents, solvents, heat transfer media, sterilants, aerosol propellants, dielectrics, fire extinguishing agents, and power cycle working fluids. Such chlorine-containing compounds have proven to be detrimental to the Earth's ozone layer. Many of the hydrofluorocarbons (HFCs), used as the substitutes of CFCs, have been found to contribute to global warming. For these reasons, there is a worldwide effort to develop new compounds that are more environmentally benign while at the same time being as effective, or more effective, from a performance standpoint.

Applicants have come to appreciate that 1,1,1,2,3-pentafluoropropene (HFO-1225ye) and 1,1,1,2-tetrafluoropropene (HFO-1234yf) are each useful in one or more of the above mentioned applications. Accordingly, compositions containing either or both fluorinated olefins are among the materials being developed for such use.

Methods for producing HFO-1234yf and HFO-1225ye are known. In one example, it is known that hexafluoropropylene (HFP) can be hydrogenated to produce 1,1,1,2,3,3-hexafluoropropane (HFC-236ea). HFC-236ea is then used as a reactant in a dehydrogenation reaction to produce HFO-1225ye. It is further known that HFO-1225ye can be hydrogenated to produce 1,1,1,2,3-pentafluoropropane (HFC-245eb) and that HFC-245eb can then be dehydrofluorinated to produce HFO-1234yf.

U.S. Pat. No. 8,013,194, the contents of which are incorporated by reference herein, further provides that HFO-1225ye and HFO-1234yf can be produced in a single facility. Most notably, it was realized that the hydrogenation of HFP can yield both HFC-236ea and HFC-245eb and that these two products can be simultaneously dehydrofluorinated to produce HFO-1225ye and HFO-1234yf, respectively. Processing conditions are taught to be adjustable, so as to favor the selective conversion of one hydrofluoroolefin over the other. Catalysts that may be used for such reactions were taught to include metal catalysts, even more preferably one or more transition metal-based catalysts (including in certain preferred embodiments transition metal halide catalysts), such as $FeCl_3$, chromiumoxyfluoride, Ni (including Ni mesh), $NiCl_2$, $CrF_3$, and mixtures thereof, supported or in bulk. Other catalysts include carbon-supported catalysts, antimony-based catalysts (such as $SbCl_5$), aluminum-based catalyst (such as $AlF_3$, $Al_2O_3$, and fluorinated $Al_2O_3$), palladium-based catalysts, platinum-based catalysts, rhodium-based catalysts and ruthenium-based catalysts, including combinations thereof.

Other examples of methods for the production of HFO-1225ye and HFO-1234yf are set forth in, at least, U.S. Pat. No. 7,560,602, which is assigned to the assignee of the present invention and is incorporated herein by reference. This patent discloses a similar dehydrohalogenation process for producing 2,3,3,3-tetrafluoropropene (1234yf) and 1,1,1, 2,3-pentafluoropropene (HFO-1225ye) by catalytic dehydrofluorination of 1,1,1,2,3-pentafluoropropane (245eb) and 1,1,1,2,3,3-hexafluoropropane (HFC-236ea), respectively. Preferred dehydrohalogenation catalysts include fluorinated chromium oxide catalysts, aluminum fluoride catalysts, ferric fluoride catalysts, mixtures of magnesium fluoride and aluminum fluoride catalysts, nickel-based catalysts, carbon based catalysts, and combinations thereof.

Alternative agents for such dehydrohalogenation reactions are also known. U.S. Patent Application Publication No. 20100029997, for example, teaches the production of hydrofluoroolefins (e.g. HFO-1234yf) by dehydrohalogenating HFC-245eb by contacting it to potassium hydroxide (KOH), sodium hydroxide (NaOH), $Ca(OH)_2$, CaO, and combinations thereof. While, in certain embodiments, dehydrohalogenation agents include KOH, alternative agents also include LiOH, $Mg(OH)_2$ and NaOH.

Applicants have come to appreciate that in commercial production or large scale production of fluorocarbons, such as HFO-1234yf and HFO-1225ye, reactions utilizing hydrogen present significant challenges. Hydrogenation reactions are typically highly exothermic, which creates challenges for thermal management of a large reactor system, particularly at a commercial or large manufacturing scale. Also, the ability to effectively utilize hydrogen to achieve a high conversion of the starting material is critical to an economic process. Safety in dealing with hydrogenation processes is also critical, as the temperatures of the reaction can easily reach extremely high, and unsafe, levels.

SUMMARY OF THE INVENTION

The present invention relates, at least in part, to methods of increasing the cost efficiency and improving the safety for halogenation production of a fluorinated alkane using a fluorinated olefin starting reagent, and in further embodiments to the use of such alkanes in the production of desired fluorinated olefin products.

In certain non-limiting embodiments, the present invention relates to methods for producing at least one halogenated alkane by first providing a starting material stream comprising at least one halogenated alkene according to Formula (I)

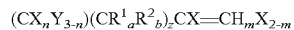

and at least one halogenated alkane according to Formula (II)

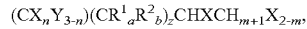

where: each X is independently Cl, F, I or Br, provided that at least two Xs are F; each Y is independently H, Cl, F, I or Br; each $R^1$ is independently H, Cl, F, I, Br or unsubstituted or halogen substituted methyl or ethyl radical; each $R_2$ is independently H, Cl, F, I, Br or unsubstituted or halogen substituted methyl or ethyl radical; n is 1, 2 or 3; a and b are each 0, 1 or 2, provided that a+b=2; m is 0, 1 or 2; and z is 0, 1, 2 or 3. In certain non-limiting aspects, the ratio of the halogenated alkene to the halogenated alkane of the starting material feed stream is from about 1:3 to about 1:25, in further aspects from about 1:6 to about 1:22, and in even further aspects from about 1:8 to about 1:20.

The starting material is then hydrogenated to produce an intermediate material stream by contacting said starting material stream with a reducing agent (e.g. $H_2$) such that at least a portion of the alkene of Formula I is converted to the alkane of Formula II. In certain non-limiting aspects, the hydrogenation step results in a percent conversion of the alkene in the starting material feed stream of between about 25 wt. % and about 75 wt. %, in certain preferred embodiments between about 35 wt. % and about 65 wt. %, in further preferred embodiments between about 40 wt. % and about 60 wt. %, and in even further preferred embodiments between about 45 wt. % and about 55 wt. %.

The intermediate product stream is then separated into at least a first intermediate product stream comprising the alkene of formula I and the alkane of formula II and a second intermediate product stream comprising the alkene of formula I and the alkane of formula II. The first intermediate product stream is then recycled to the first reactor. In certain embodiments, prior to being recycled the first intermediate product stream is mixed with additional starting material (i.e. additional halogenated alkene), thereby, adjusting the ratio of the fluorinated alkene to the fluorinated alkane. In certain non-limiting aspects, the additional starting material is provided such that the resulting ratio of the fluorinated alkene to the fluorinated alkane in the first intermediate product stream is from about 1:3 to about 1:25, in certain preferred embodiments the ratio is from about 1:6 to about 1:22, and in further preferred embodiments the ratio is from about 1:8 to about 1:20.

The second intermediate product stream is then further hydrogenated in a second reactor to produce a final product stream. In certain non-limiting embodiments, the final product stream comprises less than 20 ppm of the fluorinated alkene of formula I, in certain preferred embodiments less than 200 ppm of the fluorinated alkene of formula I, and in further preferred embodiments less than 2,000 ppm of the fluorinated alkene of formula I. The resulting product stream may be stored or otherwise processed. In certain preferred embodiments, it is dehydrohalogenated to produce a second fluorinated olefin of formula I, wherein, in certain aspects, the second fluorinated olefin of formula I has one less fluorine atom than the starting fluorinated olefin.

In certain non-limiting aspects, one or both of the hydrogenation reaction above, or otherwise herein, are conducted, at least in part, in a liquid phase. Such reaction may also be conducted in the present of a catalyst, which may be selected from the group consisting of Pd on carbon, Pd/$\alpha$-Al$_2$O$_3$, Ni/C, and Ni/Al$_2$O$_3$.

In additional embodiments, the present invention relates to methods for producing a fluorinated alkane by providing a starting material stream comprising hexafluoropropene and 1,1,1,2,3,3-hexafluoropropane. In certain non-limiting aspects, the ratio of hexafluoropropene and 1,1,1,2,3,3-hexafluoropropane in the starting material stream is from about 1:3 to about 1:25, in certain preferred embodiments the ratio is from about 1:6 to about 1:22, and in further preferred embodiments the ratio is from about 1:8 to about 1:20.

The starting material is then hydrogenated with a reducing agent (e.g. H$_2$) such that at least a portion of said hexafluoropropene is converted to 1,1,1,2,3,3-hexafluoropropane and to produce an intermediate stream comprising hexafluoropropene and 1,1,1,2,3,3-hexafluoropropane. In certain non-limiting aspects, the hydrogenation step results in a percent conversion of the hexafluoropropene of between about 25 wt. % and about 75 wt. %, in certain preferred embodiments between about 35 wt. % and about 65 wt. %, in further preferred embodiments between about 40 wt. % and about 60 wt. %, and in even further preferred embodiments between about 45 wt. % and about 55 wt. %.

The intermediate product stream is then separated into a first intermediate product stream comprising hexafluoropropene and 1,1,1,2,3,3-hexafluoropropane and a second intermediate product stream comprising hexafluoropropene and 1,1,1,2,3,3-hexafluoropropane. To the first intermediate product stream additional hexafluoropropene may be added, such that the ratio of the hexafluoropropene to the hexafluoropropene is from about 1:3 to about 1:25, in further aspects from about 1:6 to about 1:22, and in even further aspects from about 1:8 to about 1:20. The first intermediate is then recycled to the hydrogenation reactor.

The second intermediate stream is then hydrogenated in a second hydrogenation reactor to produce a final product stream. In certain non-limiting embodiments, the final product stream comprises less than 20 ppm of hexafluoropropene, in certain preferred embodiments less than 200 ppm of hexafluoropropene, and in further preferred embodiments less than 2,000 ppm of hexafluoropropene. This product stream may be stored, or in certain embodiments, dehydrohalogenated to form 1,2,3,3,3-pentafluoropropene.

In further aspects, the present invention relates to methods for producing a fluorinated alkane by providing a starting material stream comprising 1,2,3,3,3-pentafluoropropene and 1,1,1,2,3-pentafluoropropane. In certain non-limiting aspects, the ratio of 1,2,3,3,3-pentafluoropropene and 1,1,1,2,3-pentafluoropropane in the starting material stream is from about 1:3 to about 1:25, in certain preferred embodiments the ratio is from about 1:6 to about 1:22, and in further preferred embodiments the ratio is from about 1:8 to about 1:20.

The starting material is then hydrogenated with a reducing agent (e.g. H$_2$) such that at least a portion of said 1,2,3,3,3-pentafluoropropene is converted to 1,1,1,2,3-pentafluoropropane and to produce an intermediate stream comprising 1,2,3,3,3-pentafluoropropene and 1,1,1,2,3-pentafluoropropane. In certain non-limiting aspects, the hydrogenation step results in a percent conversion of the 1,2,3,3,3-pentafluoropropene of between about 25 wt. % and about 75 wt. %, in certain preferred embodiments between about 35 wt. % and about 65 wt. %, in further preferred embodiments between about 40 wt. % and about 60 wt. %, and in even further preferred embodiments between about 45 wt. % and about 55 wt. %.

The intermediate product stream is then separated into a first intermediate product stream comprising 1,2,3,3,3-pentafluoropropene and 1,1,1,2,3-pentafluoropropane and a second intermediate product stream comprising 1,2,3,3,3-pentafluoropropene and 1,1,1,2,3-pentafluoropropane. To the first intermediate product stream additional 1,2,3,3,3-pentafluoropropene may be added, such that the ratio of the 1,2,3,3,3-pentafluoropropene to the 1,1,1,2,3-pentafluoropropane is from about 1:3 to about 1:25, in further aspects from about 1:6 to about 1:22, and in even further aspects from about 1:8 to about 1:20. The first intermediate is then recycled to the hydrogenation reactor.

In certain non-limiting embodiments, the final product stream comprises less than 20 ppm of 1,2,3,3,3-pentafluoropropene, in certain preferred embodiments less than 200 ppm of 1,2,3,3,3-pentafluoropropene, and in further preferred embodiments less than 2,000 ppm of 1,2,3,3,3-pentafluoropropene. This product stream may be stored, or in certain embodiments, dehydrohalogenated to form 2,3,3,3-tetrafluoropropene Additional embodiments and advantages of the instant invention will be readily apparent to one of skill in the art based on the disclosure provided herein.

BRIEF DESCRIPTION OF THE DRAWINGS

FIG. 1 is a process flow diagram showing the conversion of a fluoroolefin to a fluoroalkene according to an embodiment of the present invention.

DETAILED DESCRIPTION OF THE INVENTION

Traditional processes for the production of fluorocarbons that utilize hydrogenation technology, such as in the manufacture of HFC-134a, utilize large vapor recycle streams or a large shell and tube type reactor to handle the thermal management issues of the hydrogenation step. Application of these types of technologies may be uneconomical due to large equipment sizes and difficulties in process control. The process of the present invention, at least in part, utilizes reactions that take place primarily in the liquid phase resulting in smaller and more economical large-scale equipment, more robust process control, near complete utilization of hydrogen, and an overall safer process than previously described processes.

To this end, and in certain aspects, the present invention relates, at least in part, to methods of increasing the cost efficiency and safety for hydrogenation of a fluorinated olefin, preferably in a commercial or large-scale manufacturing setting, by controlling the reaction conditions and parameters. As used herein, the term "reaction conditions" or "reaction parameters" is intended to include the singular and means control of any one or more processing parameters, including possibly using or not using a reaction vessel or stage, which can be modified by the operator of the reaction to produce the conversion and/or selectivity of the feed material in accordance with the teachings contained herein. By way of example, but not by way of limitation, conversion of the feed material may be controlled or regulated by controlling or regulating any one or more of the following: the temperature of the reaction, the flow rate of the reactants, the presence of diluent, the amount of catalyst present in the reaction vessel, the shape and size of the reaction vessel, the pressure of the reaction, and any one combinations of these and other process parameters which will be available and known to those skilled in the art in view of the disclosure contained herein.

In one aspect, the present invention relates to hydrogenation of a fluorinated olefin (e.g. a pentafluoropropene and/or hexafluoropropene) to form a fluorinated alkane (e.g. pentafluoropropane and/or hexafluoropropane), wherein the amount of the starting fluorinated olefin is diluted prior to hydrogenation with a fluorinated alkane, in preferred aspects it is diluted with at least the targeted fluorinated alkane product of the hydrogenation reaction. The reaction conditions may be controlled so as to produce a product stream wherein only a portion of the starting olefin was converted. From this product stream, a first portion, containing both the fluorinated olefin starting reactant and the fluorinated alkane product, is isolated and recycled back to the reactor. To this first portion, additional fluorinated olefin starting material may be added before it is recycled to the hydrogenation reactor. The remaining portion of the product stream, which is also comprised of fluorinated olefin and fluorinated alkane, is then provided to a second reactor for continued hydrogenation. The rate of hydrogen flow is controlled in this second reaction so as to control the fluorinated olefin conversion, temperature and pressure of the reaction. The final product produced from the second reaction may then be used or otherwise further processed, as required. In certain preferred embodiments, it is then dehydrohalogenated to produce the desired fluorinated olefin product or an intermediate product that may be further processed.

In certain embodiments, the fluorinated olefins of the present invention include one or more C3 to C6 fluoroalkenes, preferably compounds having a formula as follows:

$$X^1CF_zR_{3-z}$$

where $X^1$ is a C2, C3, C4, or C5 unsaturated, substituted or unsubstituted, alkyl radical, each R is independently Cl, F, Br, I or H, and z is 1 to 3. Highly preferred among such compounds are propenes and butenes having from 3 to 5 fluorine substituents, and among these tetrafluoropropenes (HFO-1234) and pentafluoropropenes (HFO-1225) are especially preferred.

In one embodiment, the process for producing the fluorinated olefins of the present invention include reacting a fluorinated olefin starting material with a degree of halogen substitution of N+1 having substantially the same number of carbon atoms as the fluorinated olefin(s) to be synthesized with a degree of halogen substitution of N. The fluorinated olefin starting material preferably, though not exclusively, has a degree of fluorine substitution of N+1 and is exposed to reaction conditions effective to produce a reaction product containing one or more fluorinated alkanes having the same number of carbons atoms as the final olefin. This olefin conversion step includes a reaction that is sometimes referred to herein for convenience, but not necessarily by way of limitation, as a reduction or hydrogenation step. The resulting fluorinated alkane is then converted to a fluorinated olefin having a degree of fluorine substitution of N. This alkane conversion step comprises a reaction that is sometimes referred to herein for convenience, but not necessarily by way of limitation, as a dehydrohalogenation reaction or more particularly in certain embodiments as a dehydrofluorination or dehydrochlorination reaction.

Based on the foregoing, in one aspect of the present invention, the process for producing a fluoroolefin includes the following steps:

(a) hydrogenating a compound of formula (I):

$$(CX_nY_{3-n})(CR^1{}_aR^2{}_b)_zCX=CH_mX_{2-m} \qquad (I)$$

under conditions effective to form at least one fluorinated alkane of formula (II)

$$(CX_nY_{3-n})(CR^1{}_aR^2{}_b)_zCHXCH_{m+1}X_{2-m} \qquad (II)$$

where:
each X is independently Cl, F, I or Br, provided that at least two Xs are F;
each Y is independently H, Cl, F, I or Br;
each $R^1$ is independently H, Cl, F, I, Br or unsubstituted or halogen substituted methyl or ethyl radical;
each $R_2$ is independently H, Cl, F, I, Br or unsubstituted or halogen substituted methyl or ethyl radical;
n is 1, 2 or 3;
a and b are each 0, 1 or 2, provided that a+b=2;
m is 0, 1 or 2; and
z is 0, 1, 2 or 3; and (b) dehydrohalogenating the compound of formula (II) under conditions effective to produce a fluoroolefin with a lower degree of fluorine substitution than the compound of formula (I), preferably to produce a compound of formula (III):

$$(CX_nY_{3-n})(CR^1{}_aR^2{}_b)_zCX=CH_{m+1}X_{1-m} \qquad (III)$$

where each n is the same value as in formula (I) and m is 0 or 1.

In further non-limiting embodiments, the reactant of formula (I) may include a three carbon olefin of formula (IA) wherein z is 0, namely $$CX_nY_{3-n}CX=CH_mX_{2-m} \qquad (IA)$$

to produce a three carbon alkane of formula (IIA) as follows:

$$(CX_nY_{3-n})CHXCH_{m+1}X_{2-m} \qquad (IIA)$$

where X, Y, n, and m are all as indicated above, which compound is then dehydrohalogenated to form a compound of formula (IIIA)

$$(CX_nY_{3-n})CX=CH_{m+1}X_{1-m} \qquad (IIIA)$$

where n is the same value as in formula (IA) and m is 0 or 1.

In even further embodiments, the instant invention provides a saturated terminal carbon of the compounds of formulas (I) or (IA) that is fully substituted with fluorine (for example, n on the saturated terminal carbon is 3 and each X on that carbon is F). In such embodiments, the compound of Formula (I) or (IA) is preferably a fluoropropene having from three to six fluorine substituents, and potentially other halogen substituents, including for example hexafluoropropene (that is, Z is 0, n is 3, m is 0, and all X are F) or pentafluoropropene (that is, Z is 0, n is 3, m is 1, and all X are F). The resulting compound of formula (II) or (IIA) is selected from the group consisting of, one or more of the following fluorinated alkanes: pentafluoropropane (HFC-245) and hexafluoropropane (HFC-236), including all isomers of each of these, but preferably 1,1,1,2,3-pentafluoropropane (HFC-245eb), 1,1,1,2,3,3-hexafluoropropane (HFC-236ea) and combinations of these. In certain preferred embodiments the fluorinated alkane produced by the conversion step has a degree of fluorine substitution of N+1.

In any of the foregoing reactions, the step wherein the olefin is converted to an alkane is carried out under conditions effective to provide a formula (I) conversion of at least about 40%, more preferably at least about 55%, and even more preferably at least about 70%. In certain preferred embodiments the conversion is at least about 90%, and more preferably about 99%. Further in certain preferred embodiments, the conversion of the compound of formula (I) or (IA) to produce a compound of formula (II) is conducted under conditions effective to provide a formula (II) or (IIA) selectivity of at least about 60%, more preferably at least about 80%, and more preferably at least about 90%, and even more preferably about 100%.

In any of the foregoing reactions, the step wherein the alkane is converted to a fluorinated olefin having a degree of fluorination of N is carried out under conditions effective to provide a formula (II) conversion of at least about 40%, more preferably at least about 55%, and even more preferably at least about 70%. In certain preferred embodiments the conversion is at least about 90%, and more preferably about 95%. Further in certain preferred embodiments, the conversion of the compound of formula (II) to produce a compound of formula (III) is conducted under conditions effective to provide a formula (III) selectivity of at least about 60%, more preferably at least about 80%, and more preferably at least about 90%, and even more preferably about 98%.

The Hydrogenation Step

Although it is contemplated that the hydrogenation or reduction step may be conducted in batch operation, it is preferred that the hydrogenation reaction is carried out as a substantially continuous operation. While it is further contemplated that the hydrogenation reaction may be conducted in a single reaction vessel, in certain preferred embodiments this reaction step may comprise two or more reactors or reaction stages in parallel, in series, or both, or any combination of reactor designs. In addition, it is contemplated that the reaction step may include one or more feed preheating or precooling steps or stages, depending on the particulars of each application.

While it is possible that the reaction may involve in certain embodiments a liquid phase reaction, a vapor phase reaction or combinations of both, it is contemplated that in certain embodiments the hydrogenation reaction comprises at least liquid phase reaction stage, and in certain preferred embodiments at least two stages of liquid phase reactions.

In certain non-limiting embodiments, and referring to FIG. 1, the hydrogenation reaction is provided within a system 1 that includes at least a first hydrogenation reactor 10 and a second hydrogenation reactor 20 for the hydrogenation of the fluorinated olefin to form the fluorinated alkane. The starting feed stream 5 is provided to the first reactor 10 from a starting source, such as a feed drum 15. Prior to entering the first reactor 10, the starting feed stream of fluorinated olefin is diluted with a fluorinated alkane product. In certain preferred embodiments, such an alkane comprises, consists essentially of, or consists of the targeted fluorinated alkane produced by the hydrogenation of the starting fluorinated olefin.

In certain aspects, such as at the initiation of the reaction, the starting feed stream may be provided with fluorinated olefin that has already been diluted with the fluorinated alkane. In further aspects, however, the fluorinated olefin is provided from the source (e.g. feed drum) in a substantially pure form and is diluted with product stream recycled from the first reactor 10, such as that depicted at reference number 25 of FIG. 1 and discussed in greater detail below. By way of non-limiting example, in an embodiment where the starting feed stream includes hexafluoropropene, the feed stream is diluted with at least 1,1,1,2,3,3-hexafluoropropane (HFC-236ea). In embodiments where the starting feed stream is 1,2,3,3,3-pentafluoropropene (HFO-1225ye), it is diluted with at least 1,1,1,2,3-pentafluoropropane (HFC-245eb).

The ratio of fluorinated olefin to fluorinated alkane in the diluted feed stream may be any amount that is effective to control one or more parameters of the reaction, such as, but not limited to, the temperature inside the reactor, the selectivity of the product produced, the conversion percentage or conversion rate of the product, or the like. Preferably, the hydrogenation reaction conditions are controlled in the reaction in order to achieve the desired conversion percentage of the fluorinated olefin and/or selectivity of the targeted fluorinated alkane in accordance with the present invention. In certain non-limiting embodiments, the ratio of fluorinated olefin to fluorinated alkane in the feed stream provided to the first reactor ranges from about 1:3 to about 1:25, in certain preferred embodiments from about 1:6 to about 1:22; in further preferred embodiments from about 1:8 to about 1:20. It is to be understood, however, that such ratio are not necessarily limiting and may be adjusted, based on the reaction performed and the desired outcome (e.g. conversion percentage, selectivity percentages, maximizing dissolution of hydrogen in the reaction mass [i.e. if $H_2$ is not too soluble, the fluorinated alkane is increased so as to increase the amount in which the $H_2$ will dissolve] and the like).

Prior to entering the first reactor, the diluted fluorinated olefin feed stream is mixed with a hydrogen feed stream 35. The amount of hydrogen provided may be any amount that is effective to control one or more of the temperature of the reaction, the temperature inside the reactor, the selectivity of the product produced, the conversion percentage or conversion rate of the product, or the like. In certain non-limiting embodiments, the hydrogen feed is provided in excess of the amount of starting fluorinated olefin. That is, in certain aspects, the ratio of hydrogen to fluorinated olefin is greater than 1:1. The fluorinated olefin feed and hydrogen may be mixed before the reaction using standard means, such as, but not limited to, a static mixer 36. In other embodiments, the ratio of hydrogen to fluorinated olefin is less than 1:1. It is to be understood, however, that such ratio are not necessarily limiting and may be adjusted, based on the reaction performed and the desired outcome (e.g. temperature control, conversion percentage, selectivity percentages, condition of the feed to second reactor, and the like).

Also prior to entering the first reactor, the temperature of the diluted olefin/hydrogen feed stream may be optionally controlled by passing it through a cooling element 30. Such cooling element is used to cool the temperature of the reactants into the first reactor as the temperature of recycle stream 50 is hotter than the desired first reactor inlet temperature due to the exothermic nature of the hydrogenation reaction. Since the reduction or hydrogenation reaction of the present invention is generally exothermic, and usually substantially exothermic, the use of such cooled material has the effect in preferred embodiments of maintaining the reactor temperature below that which would exist if the recycle were not used, assuming all other process conditions were maintained the same.

As illustrated in FIG. 1, however, the present invention is not limited to the inclusion of a precooling step and may also include a by-pass 40 of the cooling element directly to the reactor 10, particularly if the feed stream is at a desired temperature or within a desired temperature range.

The hydrogenation reaction can be catalyzed using any hydrogenation catalyst, and in certain embodiments a liquid phase hydrogenation catalyst. According to certain preferred embodiments of the invention, carbon or alpha-alumina supported metal catalysts are employed in the hydrogenation of fluoroolefins to hydrofluorocarbons. Non-limiting examples of metal components include Pd, Ru, Pt, Rh, Ir, Fe, Co, Ni, Cu, Ag, Re, Os, Au, and any combinations thereof. The metal loading can vary within a large range, e.g., from 0.1-10 wt %. However, for noble metals such as Ru, Ph, Pd, Pt, Ir, etc., the metal loading is preferably about 0.1 to about 5 wt %, and more preferably about 0.1 to about 1 wt %. It has been discovered that supported catalyst having metal concentrations below about 0.1 wt. % are not highly effective at hydrogenating fluoroolefins or hydrofluoroolefins. Preferably, though not exclusively, the hydrogenation catalyst is selected from the group consisting of Pd on carbon, Pd/$\alpha$-Al$_2$O$_3$, Ni/C, and Ni/Al$_2$O$_3$ While it is contemplated that a wide variety of hydrogenation reaction temperatures may be used, depending on relevant factors such as the catalyst being used and the most desired reaction product, it is generally preferred that such conditions be controlled so as to provide the reaction in a liquid phase. To this end, and in certain non-limiting aspects, the reaction temperature for the hydrogenation step is from about 10° C. to about 500° C., preferably about from 25° C. to about 400° C., and even more preferably from about 50° C. to about 300° C.

It is further contemplated that a wide variety of reaction pressures may be used. In the aspects of the invention, however, the pressure within the first reactor may be such that hydrogenation reaction is conducted substantially in the liquid phase. Such pressures may include, for example, from about 100 psig to about 1,500 psig and in certain preferred embodiments from about from 200 psig to about 1,000 psig.

Again, in certain preferred aspects, the hydrogenation of the fluorinated olefin in the first reactor is limited so as to control the exothermic nature of the reaction, and thereby the temperature within the reactor. Hydrogenation reactions, by nature, are highly exothermic. This is particularly true with the conversion of HFP to HFC-236ea and HFO-1225ye to HFC-245eb, as illustrated by the negative enthalpy values below.

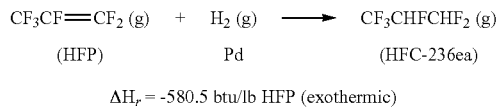

$\Delta H_r$ = -580.5 btu/lb HFP (exothermic)

-continued

$\Delta H_r$ = -457 btu/lb HFO-1225ye (exothermic)

Accordingly, and in addition to one or more of the parameters above, the temperature within the reactor is also controlled by limiting the contact time of the fluorinated olefin, H$_2$ and the catalyst. Such contact times may include but are not limited to from about 1 to about 180 seconds preferably from about 5 to about 60 seconds. The present invention is not limited the foregoing, and such times may also include any amount to keep the reactor within commercially tolerable temperature levels.

In certain non-limiting embodiments, however, the contact times, temperature, pressure, reactant flow/concentration, etc. are controlled to result in a percent conversion of the fluorinated olefin is between about 25 wt. % and about 75 wt. %; in certain preferred embodiments between about 35 wt. % and about 65 wt. %; in further preferred embodiments between about 40 wt. % and 60 wt. %; in even further preferred embodiments between about 45 wt. % and about 55 wt. % and in even further preferred embodiments about 50 wt. %.

The product stream emerging from the reactor 10 is then divided where a first portion 45 of it is provided to a second reactor for further processing and the remaining (or second) portion is recycled 50. The flow of the latter, recycled portion is controlled to contain an effective amount of fluorinated olefin and fluorinated alkane product, such that when it is combined with the pure fluorinated olefin feed stream at point 25, the resulting level of the diluted fluorinated olefin will be in accordance with that above. To this end, and in certain preferred embodiments, the level of fluorinated olefin in the recycled portion is such that, when it is combined with additional fluorinated olefin, the resulting ratio of fluorinated olefin to fluorinated alkane in the feed stream provided to the first reactor may ranges from about 1:3 to about 1:25, in certain preferred embodiments from about 1:6 to about 1:22; in further preferred embodiments from about 1:8 to about 1:20.

While a myriad of other factors also may be used to determine how much of the product stream is recycled 45 and how much is fed to the second reactor for further hydrogenation, in certain aspects, the amount of recycle is determined by the degree of exotherm (i.e. the temperature of the product stream) that can be tolerated by the system. In certain non-limiting aspects, it is desirable to maintain the temperature of the product stream to less than about 200° C., in certain preferred aspects to less than about 100° C., in further aspects to less than about 50° C., and in even further aspects to less than about 35° C. To this end, the amount of product stream that is recycle is such that the resulting product of the recycle can be maintained to within these temperatures.

The portion of the feed stream that is not recycled 45, is then feed to the second reactor 20 for further hydrogenation and to react the remaining fluoroolefin down to very low concentration levels. In certain non-limiting embodiments, the ratio of fluorinated olefin to fluorinated alkane in the feed stream provided to the second reactor ranges from about 1:3 to about 1:25, in certain preferred embodiments from about 1:6 to about 1:22; in further preferred embodiments from about 1:8 to about 1:20. It is to be understood, however, that such ratio are not necessarily limiting and may be adjusted, based on the reaction performed and the desired outcome (e.g. conversion percentage, selectivity percentages, and the like).

Prior to entering the second reactor 20, the diluted fluoroolefin feed stream 45 is provided with hydrogen feed stream 55, and may be mixed using standard means, such as, but not limited to, a static mixer 66. The amount of hydrogen may be any amount to control the temperature of the reaction, desired rate of conversion, or the like. To this end, and in certain preferred embodiments, the feed rate of hydrogen, amount/dilution of the fluorinated olefin, reaction parameters, and the like is controlled to result in a conversion rate that is greater than, and preferably substantially greater than, the conversion rate in the first reaction stage. In certain preferred embodiments, for example, the conversion percentage in the second reaction stage is from about 20% to about 99%. In further preferred embodiments, the conversion in the second reaction stage is preferably greater than 95%, and even more preferably about 100%. To this end, and in certain preferred embodiments, the product stream exiting the second reactor 20 may have a level of unreacted fluorinated olefin of less than 20 ppm, preferably less than 200 ppm, and most preferably to less than 2,000 ppm.

Also prior to entering the second reactor, the temperature of the diluted olefin/hydrogen feed stream may be optionally controlled by passing it through a cooling element 65. Such cooling element is used to control the temperature of the reactants into the second reactor as feed stream 45, which came directly out of the 1$^{st}$ reactor, is hotter than the desired second reactor inlet temperature due to the exothermic nature of the hydrogenation reaction. Since the reduction or hydrogenation reaction of the present invention is generally exothermic, and usually substantially exothermic, the use of such cooled material has the effect in preferred embodiments of maintaining the reactor temperature below that which would exist if the cooling element were not used, assuming all other process conditions were maintained the same.

As illustrated in FIG. 1, the present invention is not limited to such an aspect and may also include a by-pass 70 to the cooling element directly to the reactor 20, particularly if the feed stream is at a desired temperature or within a desired temperature range.

The hydrogenation reaction in the second reactor can be catalyzed using any hydrogenation catalyst. According to a preferred embodiment of the invention, carbon or alpha-alumina supported metal catalysts are employed in the hydrogenation of fluoroolefins to hydrofluorocarbons. Non-limiting examples of metal components include Pd, Ru, Pt, Rh, Ir, Fe, Co, Ni, Cu, Ag, Re, Os, Au, and any combinations thereof. The metal loading can vary within a large range, e.g., from 0.1-10 wt %. However, for noble metals such as Ru, Ph, Pd, Pt, Ir, etc., the metal loading is preferably about 0.1 to about 5 wt %, and more preferably about 0.1 to about 1 wt %. It has been discovered that supported catalyst having metal concentrations below about 0.1 wt. % are not highly effective at hydrogenating fluoroolefins or hydrofluoroolefins. Preferably, though not exclusively, the hydrogenation catalyst is selected from the group consisting of Pd on carbon, Pd/α-$Al_2O_3$, Ni/C, and Ni/$Al_2O_3$.

While it is contemplated that a wide variety of hydrogenation reaction temperatures may be used, depending on relevant factors such as the reactant fluoroolefin, heat of reaction, catalyst being used and the most desired reaction product, it is generally preferred that such conditions be controlled so as to provide the reaction in a liquid phase. To this end, and in certain non-limiting aspects, the reaction temperature for the hydrogenation step is from about 10° C. to about 500° C., preferably about from 25° C. to about 400° C., and even more preferably from about 50° C. to about 300° C.

It is further contemplated that a wide variety of reaction pressures may be used, again, in the aspects of the invention the pressure within the first reactor may be such that hydrogenation reaction is conducted in the liquid phase. The reaction pressure can be, for example, from about 100 psig to about 1,500 psig and in certain preferred embodiments from about from 200 psig to about 1,000 psig.

The product steam exiting the second reactor 20, can then be optionally cooled by a cooling element 80. In certain aspects, it may be optionally cooled to any final temperature that is desirable for additional processing, end processing, storage, or any other use for the products produced during the reaction. In certain preferred aspects, the product stream is cooled to a temperature from about 20° C. to about 100° C., more preferably from about 20° C. to about 90° C., and most preferably from about 20° C. to about 70° C., which is optimal for dehydrohalogenation (discussed below).

The size and shape, and other characteristics of the reaction vessels (e.g. first and second reactors) may vary widely with the scope of the present invention, and it is contemplated that the vessel associated with each stage may be different than or the same as the vessel associated with the upstream and downstream reaction stages. Furthermore, it is contemplated that all reaction stages can occur inside a single vessel, provided that means and mechanisms necessary to control conversion are provided in accordance with the above. For example, it may be desirable in certain embodiments to utilize a single tubular reactor for each reaction stage, providing conversion control by judicious selection of the amount and/or distribution of catalyst throughout the tubular reactor. In such a case, it is possible to further control the conversion in different sections of the same tubular reactor by controlling the amount of heat removed from or added to different sections of the tubular reactor. Means to remove heat are known in the art and include interstage cooling of a portion of the flow and returning to the main flow; cold shot liquid wherein an amount of reaction product is injected into the intermediate stream.

Dehydrohalogenation

In certain non-limiting aspects of the invention, the final fluorinated alkane product stream exiting the second reactor is dehydrohalogenated to produce a fluorinated olefin having one less fluorine atom that the starting olefin. This dehydrofluorination step can be carried out in a liquid phase in the presence of a dehydrohalogenation agent (e.g. caustic solution) or a gas phase in the presence of a dehydrofluorination catalyst. It is contemplated that the reaction may be carried out batchwise, continuously or a combination thereof.

In one embodiment the converting step involves a reaction in which the fluorinated alkane (e.g. HFC-245eb and/or HFC-236ea) is contacted with a dehydrohalogenating agent such as KOH, NaOH, Ca(OH)$_2$, LiOH, Mg(OH)$_2$, CaO, and combinations thereof to form the fluorinated olefin. By way of example, if KOH is used, such a reaction may be described by way of illustration, but not necessarily by way of limitation, by the following reaction equations (1) and (2):

$$CF_3-CHF-CHF_2+KOH \rightarrow CF_3CF=CHF+KF+H_2O \quad (1)$$

$$CF_3-CHF-CH_2F+KOH \rightarrow CF_3CF=CH_2+KF+H_2O \quad (2)$$

The dehydrohalogenating agent may be provided as a caustic aqueous solution comprising from about 2% to about 100%, more preferably from about 10% to about 50%, and even more preferably from about 10% to about 50% by weight of dehydrohalogenating agent. In further embodiments, the caustic solution, and preferably the dehydrohalogenating agent solution, is brought to a temperature of from about 20° C. to about 100° C., more preferably from about 20° C. to about 90° C., and most preferably from about 20° C. to about 70° C. The reaction pressure in such embodiments may vary, depending on particular processing parameters of each application. In certain embodiments, the reaction pressure ranges from atmospheric pressure, super-atmospheric pressure or under vacuum. The vacuum pressure, when used, in certain embodiments ranges from about 5 torr to about 760 torr.

It is contemplated that the amount of dehydrohalogenation agent (or reagent) used, or mole ratio of reagent to organic, will vary depending on the particular parameters present in each embodiment. In certain embodiments, the mol ratio of dehydrohalogenating agent to fluorinated alkane is from less than 1 to 3, preferably 1-1.5. In further embodiments, the contact time, which is expressed as the ratio of the volume of the reagent (ml) to the total feed flow (ml/sec) is from about 0.1 seconds to about 1000 seconds, and preferably from about 2 seconds to about 120 seconds.

The dehydrohalogenation reactions can be accomplished using any suitable vessel or reactor. Such vessels or reactors should be constructed from materials which are resistant to corrosion, such as stainless steel, nickel and its alloys, including Hastelloy, Inconel, Incoloy, and Monel. In certain embodiments, this reaction is performed using one or a series of Continuously Stirred Tank Reactors (CSTR). In this type of reactor, fluorinated alkane feed and dehydrohalogenating agent would be fed continuously into the reactor and the resulting product stream formed would be fed into a condenser or distillation column for separation of fluorinated olefin product (e.g. 1225ye and/or 1234yf) from and unreacted fluorinated alkane, as well as other by-products of the reaction.

In certain embodiments, spent dehydrohalogenating agent is removed from the product stream either periodically or continuously and is recycled back to the reactor for reuse. As noted previously, Applicants have discovered that, during continuous processing the reaction proceeds until either the fluorinated alkane reactants or dehydrohalogenating agent is consumed. This increases costs of productivity because the reactor must be dismantled upon completion of the reaction to remove the salt and/or salt solutions. By recycling the dehydrohalogenating agent and by-product salts, however, such costs may be reduced and the system made more efficient.

Spent dehydrohalogenating agent and by-product salts (e.g. metal fluoride salts) may be withdrawn from the reactor by a product stream either continuously or intermittently using one or more known separation techniques. To this end, spent dehydrohalogenating agent separation may occur using any known compound separation techniques, such, but not limited to, distillation, phase separation, etc. In certain embodiments, withdrawal of spent dehydrohalogenating agent is especially beneficial for component separation as it allows for facile separation of organic and dehydrohalogenating agent. This in turn leads to lower cost associated with design and operation of complicated and highly specialized separation equipment.

The product stream containing spent dehydrohalogenating agent typically carries with it some dissolved fluorinated alkane. By stopping the stirrer and then removing spent dehydrohalogenating agent during the time agitation is stopped, separation of dehydrohalogenating agent and such alkane can be facilitated. Spent dehydrohalogenating agent and dissolved alkane would be taken into a container where additional separation of dehydrohalogenating agent and alkane can be accomplished using one or more of the foregoing separation techniques. In one non-limiting embodiment, for example, KOH is separation by distillation, i.e. by heating the alkane just above its boiling point, thus fractionating it from the spent KOH. Alternatively, one can use phase separator to separate between the two phases. The organic free KOH isolate can be immediately recycled to the reactor or can be concentrated and the concentrated solution can be returned to reactor.

The by-product salt can also be isolated and converted back to the dehydrohalogenating agent used known methods. When KOH is used as the dehydrohalogenating agent, for example, KF is formed as a by-product salt. Such salt may be converted back to KOH and recycled back to the dehydrohalogenation reaction. For example, $Ca(OH)_2$ can be used for KF conversion according to reaction below.

$$2KF+Ca(OH)_2 \rightarrow 2KOH+CaF_2$$

$CaF_2$ will precipitate from the foregoing reaction while KOH is isolated and recycled back to reactor. Recycling of spent dehydrohalogenating agent leads to better efficiency of the reagent use. Moreover, the use of recycling of the by-product salt reduces dehydrohalogenating agent use, reduces costs of reagents and costs associated with disposal of the salt, and/or purchase of new raw material.

In another embodiment the dehydrohalogenation step involves a reaction in which the fluorinated alkane (e.g. HFC-245eb and/or HFC-236ea) is contacted with a dehydrohalogenating catalyst in the vapor phase. The process involves the catalytic conversion of HFC-245eb and/or HFC-236ea by dehydrofluorinating HFC-245eb or HFC-236ea to form the fluorinated olefin. By way of example, if a vapor phase catalyst is used, such a reaction may be described by way of illustration, but not necessarily by way of limitation, by the following reaction equations (1) and (2):

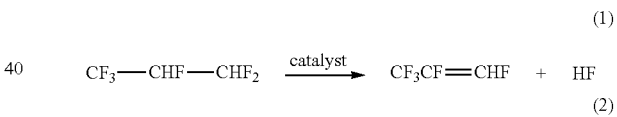

Vapor phase dehydrofluorination reactions are well known in the art. Preferably dehydrofluorination of HFC-245eb and HFC-236ea is done in a vapor phase, and more preferably in a fixed-bed reactor in the vapor phase. The dehydrofluorination reaction may be conducted in any suitable reaction vessel or reactor, but it should preferably be constructed from materials which are resistant to the corrosive effects of hydrogen fluoride such as nickel and its alloys, including Hastelloy, Inconel, Incoloy, and Monel or vessels lined with fluoropolymers. These may be single or multiple tubes packed with a dehydrofluorinating catalyst which may be one or more of fluorinated metal oxides in bulk form or supported, metal halides in bulk form or supported, and carbon supported transition metals, metal oxides and halides. Suitable catalysts non-exclusively include fluorinated chromia (fluorinated $Cr_2O_3$), fluorinated alumina (fluorinated $Al_2O_3$), metal fluorides (e.g., $CrF_3$, $AlF_3$) and carbon supported transition metals (zero oxidation state) such as Fe/C, Co/C, Ni/C, Pd/C or transition metals halides. The HFC-245eb or HFC-236ea is introduced into the reactor either in pure form, impure form, or together with an optional inert gas diluent such as nitrogen, argon, or the like. In a preferred embodiment of the invention, the HFC-245eb or HFC-236ea is pre-vaporized or preheated prior to entering the reactor. Alternately, the HFC-245eb or HFC-236ea is vaporized inside the reactor. Useful reaction temperatures may range from about 100° C. to about 600° C. Preferred temperatures may range from about 150° C. to about 450° C., and more preferred temperatures may range from about 200° C. to about 350° C. The reaction may be conducted at atmospheric pressure, super-atmospheric pressure or under vacuum. The vacuum pressure can be from about 5 torr to about 760 torr. Contact time of the HFC-245eb or HFC-236ea with the catalyst may range from about 0.5 seconds to about 120 seconds, however, longer or shorter times can be used.

The resulting products may be isolated from the product stream using one or more methods known in the art and purified accordingly.

In certain non-limiting aspects of the foregoing hydrogenation and dehydrohalogenation reactions, the starting reagents hexafluoropropene (HFP) and/or HFO-1225ye are hydrogenated to produce the fluorinated alkanes HFC-236ea and HFC-245eb, respectively. That is HFP and/or HFO-122ye are hydrogenated in accordance with two stage reaction methods provided herein to produce a reaction produced comprising HFC-236ea and/or HFC-245eb. HFC-236ea is then dehydrohalogenated to produce HFO-1225ye, and HFC-245eb is dehydrohalogenated to produce HFO-1234yf.

In even further embodiments the hydrogenation and dehyrohalogenation steps may be performed in series to convert HFP into HFO-1234yf. That is, HFP is hydrogenated in accordance with the two stage reaction methods provided herein to produce the fluorinated alkane HFC-236ea HFC-236ea is then dehydrohalogenated to produce HFO-1225ye, which is then isolated and halogenated, in accordance with the two stage reaction methods discussed herein, to produce HFC-245eb. This alkane is then dehydrohalogenated in accordance with the methods provided herein to produce HFO-1234yf.

EXAMPLES

The following examples are provided for the purpose of illustrating the present invention but without limiting the scope thereof.

Examples 1-3

Hexafluoropropene—1$^{st}$ Stage Reaction Studies

A reactor was constructed of 2 parallel lengths of ½" SS tubing. The first length was the preheater and was heated by electrical heat tape and insulated. It was packed with nickel mesh to facilitate heat transfer and mixing. The second length had a ⅛" profile probe inserted inside it from top to bottom to monitor the catalyst bed temperature. The reactor was loaded with about 21 grams (50 cc) of Aldrich 1% Pd/C catalyst and had electrical heat tape and insulation around it for heating. The catalyst was treated prior to initial startup by flowing 200 ml/min $H_2$ over the catalyst starting at room temperature and heating up to a hot spot of 225° C. The temperature was held at 225° C. for 8 hours.

Three experiments were run using a diluted hexafluoropropene (HFP) feed in the intended product hexafluoropropane with the goal of achieving about 50% conversion of HFP while managing the heat of reaction. The experiments were run at about 290 psig and 200° C. Experiment 1 used a feed that had about 7.5 GC area % HFP. The average conversion for the 12 hour experiment was 50.5% when using a 0.55:1 mole ratio of $H_2$ to HFP. The selectivity for desired products was 98.0%. Experiment 2 used a feed that had about 12.7 GC area % HFP. The average conversion for the 10 hour experiment was 50.2% when using a 0.55:1 mole ratio of $H_2$ to HFP. The selectivity for desired products was 98.6%. Experiment 3 used a feed that had about 20.5 GC area % HFP. The average conversion for the 12 hour experiment was 57.2% when using a 0.6:1 mole ratio of $H_2$ to HFP. The selectivity for desired products was 98.4%. Temperature control within the reactor was not an issue when the goal of about 50% HFP conversion was achieved.

Experimental data can be found in Tables 1 and 2 below.

TABLE 1

GC area % of the various diluted HFP feed materials used for experiments 1-3

| Exp# | HFP | 1234yf | 1225yez | 236ea | 254iso | 245fa | 245eb | 1234ze cis | 254fb | others |
|---|---|---|---|---|---|---|---|---|---|---|
| 1 | 7.545 | 0.027 | 0.138 | 90.001 | 0.269 | 0.183 | 0.237 | 0.087 | 1.342 | 0.171 |
| 2 | 12.742 | 0.037 | 0.227 | 84.956 | 0.264 | 0.17 | 0.262 | 0.005 | 1.144 | 0.193 |
| 3 | 20.497 | 0.033 | 0.309 | 76.949 | 0.236 | 0.175 | 0.45 | 0 | 1.079 | 0.272 |

TABLE 2

Summary of HFP hydrogenation experiments 1-3

| Exp# | Pressure (Psig) | Organic feed rate (lb/hr) | H2:HFP mole ratio | Temperature (° C.) | Average HFP conversion | Average selectivity of useful products (1234yf, 1225ye, 236ea, 245eb) |
|---|---|---|---|---|---|---|
| 1 | 290 | 1.085 | 0.55 | 200 | 50.5 | 98.0 |
| 2 | 290 | 1.085 | 0.55 | 200 | 50.2 | 98.6 |
| 3 | 290 | 1.085 | 0.6 | 200 | 57.2 | 98.4 |

Example 4

Hexafluoropropene—1$^{st}$ Stage Reaction Studies

The reactor effluent stream from Example 1 is fed into a second hydrogenation reactor along with a small stoichiometric excess amount of $H_2$ compared to the total amount of olefins in the feed. The reactor design is the same as used for Example 1-3. The reactor is loaded with about 23 grams (50 cc) of Aldrich 1% Pd/C catalyst and has electrical heat tape and insulation around it for heating. The catalyst is pretreated in the same way as Example 1-3. The organic feed contains about 3.25 GC area % HFP and is fed at a rate of 0.75 lb/hr. The reactor is run at a pressure of 200° C. and at a pressure of about 300 psig. The reactor effluent is analyzed by GC and is found to contain only 0.05% HFP. The selectivity to the desired hexafluoropropane product is >98.5%.

Examples 5-7

1,2,3,3,3-Pentafluoropropene—1$^{st}$ Stage Reaction Studies

A reactor was constructed of 2 parallel lengths of ½" SS tubing. The first length was the preheater and was heated by electrical heat tape and insulated. It was packed with nickel mesh to facilitate heat transfer and mixing. The 2$^{nd}$ length had a ⅛" profile probe inserted inside it from top to bottom to monitor the catalyst bed temperature.

50 cc (20.8 grams) of fresh Aldrich 1% Pd/C were charged to the ½" OD×30" L tube reactor. The catalyst was treated prior to initial startup by flowing 200 ml/min H$_2$ over the catalyst starting at room temperature and heating up to a hot spot of 225° C. The temperature was held at 225° C. for 8 hours.

Three experiments were run using a diluted 1,2,3,3,3-pentafluoropropene (1225ye) feed in the intended product 1,1,1, 2,3-pentafluoropropane (245eb) with the goal of achieving about 50% conversion of 1225ye while managing the heat of reaction. The feed for all three experiments contained about 11.4% combined 1225ye Z and E isomers, but also contained about 2.5 GC area % of the unsaturated fluorinated olefin HFP. Experiment 1 was run at a temperature of 80° C. and at a pressure of 395 psig. The average conversions for the 8 hour experiment were 39.9% for 1225ye (combined Z and E isomer) and 99.7% for HFP when using a 0.55:1 mole ratio of H$_2$ to 1225ye/HFP combined. This was a utilization of about 96.7% of the H$_2$ fed. The selectivity for 245eb was 98.6%. Experiment 2 was run at a temperature of 200° C. and at a pressure of 395 psig. The average conversions for the 9 hour experiment were 36.2% for 1225ye (combined Z and E isomer) and 96.6% for HFP when using a 0.55:1 mole ratio of H2 to 1225ye/HFP combined. This was a utilization of about 90.6% of the H2 fed. The selectivity for 245eb was 98.9%. Experiment 3 was run at a temperature of 100° C. and at a pressure of 395 psig. The average conversions for the 9 hour experiment were 38.5% for 1225ye (combined Z and E isomer) and 99.1% for HFP when using a 0.55:1 mole ratio of H2 to 1225ye/HFP combined. This was a utilization of about 95.0% of the H$_2$ fed. The selectivity for 245eb was 99.4%. Temperature control within the reactor was not an issue when the goal of about 50% 1225ye conversion was achieved. Experimental data can be found in Tables 3 and 4 below.

TABLE 3

Feed Compositions for Exp# 1225ye-1, 1225ye-2, and 1225ye-3
GC Area %

| Exp | 1234yf | 1225yeZ | 1225yee | 254eb | 236ea | 245eb | 254fb | others |
|---|---|---|---|---|---|---|---|---|
| 1225ye-1-3 | 2.49 | 10.95 | 0.43 | 4.40 | 0.00 | 81.41 | 0.13 | 0.18 |

TABLE 4

Experimental Data Summary for Exp# 1225ye-1, 1225ye-2, 1225ye-3

| Exp# | Conditions | Overall 1225ye(Z) and 1225ye(E) Con. (molar %) | 1234yf Conv. mol % | 254eb Sel. mol % | 245eb Sel. mol % | 245fb Sel. mol % | Others Sel. mol. % | Cal. H2 consumed (%) |
|---|---|---|---|---|---|---|---|---|
| 1225ye-1 | 80 C., 395 psig, 0.55 H2/olefin | 39.9 | 99.7 | 0.8 | 98.6 | 0.6 | 0.0 | 96.7 |
| 1225ye-2 | 200 C., 395 psig, 0.55 H2/olefin | 36.2 | 96.6 | 0.6 | 98.9 | 0.5 | 0.0 | 90.6 |
| 1225ye-3 | 100 C., 395 psig, 0.55 H2/olefin | 38.5 | 99.1 | 0.0 | 99.4 | 0.6 | 0.0 | 95.0 |

Example 8

1,2,3,3,3-pentafluoropropene—2$^{nd}$ Stage Reaction Studies

The reactor effluent stream from Example 5 is fed into a 2$^{nd}$ hydrogenation reactor along with a small stoichiometric excess amount of H2 compared to the total amount of olefins in the feed. The reactor design is the same as used for Example 5-7. The reactor is loaded with about 23 grams (50 cc) of Aldrich 1% Pd/C catalyst and has electrical heat tape and insulation around it for heating. The catalyst is pretreated in the same way as Example 5-7. The organic feed contains about 6.8 GC area % HFP and is fed at a rate of 0.55 lb/hr. The reactor is run at a pressure of 100° C. and at a pressure of about 400 psig. The reactor effluent is analyzed by GC and is found to contain only 0.1% 1225yeE and 1225yeZ. The selectivity to the desired 1,1,1,2,3-pentafluoropropane (245eb) product is >98.0%.

What is claimed is:

1. A method for producing at least one fluorinated alkane comprising:
   a. providing to a first reactor a liquid phase starting material stream comprising at least one alkene according to Formula (I)

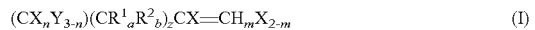

$$(CX_nY_{3-n})(CR^1_aR^2_b)_zCX=CH_mX_{2-m} \quad (I)$$

and at least one alkane according to Formula (II)

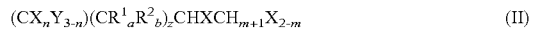

$$(CX_nY_{3-n})(CR^1_aR^2_b)_zCHXCH_{m+1}X_{2-m} \quad (II)$$

where:
   each X is independently Cl, F, I or Br, provided that at least two Xs are F;
   each Y is independently H, Cl, F, I or Br;
   each R$^1$ is independently H, Cl, F, I, Br or unsubstituted or halogen substituted methyl or ethyl radical;
   each R$_2$ is independently H, Cl, F, I, Br or unsubstituted or halogen substituted methyl or ethyl radical;
   n is 1, 2 or 3;
   a and b are each 0, 1 or 2, provided that a+b=2;
   m is 0, 1 or 2; and
   z is 0, 1, 2 or 3, wherein a ratio of the alkene of formula I to the alkane of formula II is from about 1:6 to about 1:22;
   b. hydrogenating the starting material stream to produce an intermediate material stream by contacting said starting material stream with a reducing agent such that from about 35 wt % to about 65 wt % of the alkene of Formula I is converted to the alkane of Formula II and wherein the selectivity to said alkane of Formula II is at least about 80 wt %;
   c. separating a portion of the intermediate product stream into at least a first intermediate product stream comprising the alkene of formula I and the alkane of formula II and a second intermediate product stream comprising the alkene of formula I and the alkane of formula II, wherein the ratio of the alkene of formula I to the alkane of formula II in said second intermediate product stream is from about 1:8 to about 1:20;
   d. recycling the first intermediate product stream to step b; and
   e. hydrogenating the second intermediate product stream in a second reactor to produce a final product stream.

2. The method of claim 1 wherein said reducing agent is H$_2$.

3. The method of claim 1 wherein a ratio of the fluorinated alkene to the fluorinated alkane of the starting material feed stream is from about 1:8 to about 1:20.

4. The method of claim 1 wherein step b results in a percent conversion of the fluorinated alkene in the starting material feed stream of between about 45 wt. % and about 55 wt. %.

5. The method of claim 1, further comprising adjusting a ratio of the fluorinated alkene to the fluorinated alkane in first intermediate product stream before recycling it to step b.

6. The method of claim 5 wherein a ratio of the fluorinated alkene to the fluorinated alkane of the first intermediate product is from about 1:3 to about 1:25.

7. The method of claim 5 wherein a ratio of the fluorinated alkene to the fluorinated alkane of the first intermediate product is from about 1:8 to about 1:20.

8. The method of claim 1 wherein the final product steam comprises less than 20 ppm of the fluorinated alkene of formula I.

9. The method of claim 1 wherein the final product steam comprises less than 200 ppm of the fluorinated alkene of formula I.

10. The method of claim 1 wherein said alkene of formula I comprises hexafluoropropylene or 1,2,3,3,3-pentafluoropropene.

11. The method of claim 1 wherein said alkane of formula II comprises 1,1,1,2,3,3-hexafluoropropane or 1,1,1,2,3-pentafluoropropane.

12. The method of claim 1, further comprising dehydrohalogenating said final product stream to produce a first fluorinated olefin of formula I and a second fluorinated olefin of formula I, wherein the second fluorinated olefin of formula I is different than said first fluorinated olefin of formula I.

13. The method of claim 12, wherein the second fluorinated olefin of formula I has one less fluorine atom that the first fluorinated olefin.

14. The method of claim 1, wherein the hydrogenating step (a) occurs in the presence of a catalyst selected from the group consisting of Pd on carbon, Pd/α-Al$_2$O$_3$, Ni/C, and Ni/Al$_2$O$_3$.

15. The method of claim 1, wherein the hydrogenating step (e) occurs in a liquid phase reaction.

16. The method of claim 15, wherein the hydrogenating step (e) occurs in the presence of a catalyst selected from the group consisting of Pd on carbon, Pd/α-Al$_2$O$_3$, Ni/C, and Ni/Al$_2$O$_3$.

17. A method for producing a fluorinated alkane comprising:
    a. providing a liquid phase starting material stream to a first reactor comprising hexafluoropropene and 1,1,1,2,3,3-hexafluoropropane, wherein a ratio of the hexafluoropropene to hexafluoropropane is from about 1:6 to about 1:22;
    b. hydrogenating the starting material stream with a reducing agent such that at least a portion of said hexafluoropropene is converted to 1,1,1,2,3,3-hexafluoropropane and to produce an intermediate stream comprising hexafluoropropene and 1,1,1,2,3,3-hexafluoropropane, wherein from about 35 wt % to about 65 wt % of the hexafluoropropene is converted and wherein the selectivity to said 1,1,1,2,3,3-hexafluoropropane of Formula II is at least about 80 wt %;
    c. separating a portion of the intermediate product stream into at least a first intermediate product stream comprising hexafluoropropene and 1,1,1,2,3,3-hexafluoropropane and a second intermediate product stream comprising hexafluoropropene and 1,1,1,2,3,3-hexafluoropropane;
    d. recycling the first intermediate product stream to step b; and
    e. hydrogenating the second intermediate product stream in a second reactor to produce a final product stream.

18. A method for producing a fluorinated alkane comprising:
   a. providing a liquid phase starting material stream to a first reactor comprising 1,2,3,3,3-pentafluoropropene and 1,1,1,2,3-pentafluoropropane, wherein a ratio of 1,2,3,3,3-pentafluoropropene to 1,1,1,2,3-pentafluoropropane is from about 1:6 to about 1:22;
   b. hydrogenating the starting material stream with a reducing agent such that at least a portion of said 1,2,3,3,3-pentafluoropropene is converted to 1,1,1,2,3-pentafluoropropane and to produce an intermediate stream comprising 1,2,3,3,3-pentafluoropropene and 1,1,1,2,3-pentafluoropropane, wherein from about 35 wt % to about 65 wt % of the 1,2,3,3,3-pentafluoropropene is converted and wherein the selectivity to said 1,1,1,2,3-pentafluoropropane is at least about 80 wt %;
   c. separating a portion of the intermediate product stream into at least a first intermediate product stream comprising 1,2,3,3,3-pentafluoropropene and 1,1,1,2,3-pentafluoropropane and a second intermediate product stream comprising 1,2,3,3,3-pentafluoropropene and 1,1,1,2,3-pentafluoropropane;
   d. recycling the first intermediate product stream to step b; and
   e. hydrogenating the second intermediate product stream in a second reactor to produce a final product stream.

* * * * *